United States Patent

Jegham et al.

[11] Patent Number: 5,663,173
[45] Date of Patent: Sep. 2, 1997

[54] N-[(1,4-DIAZABICYCLO[2.2.2] OCT-2-YL) METHYL] BENZAMIDE DERIVATIVES, THEIR PREPARATIONS AND THEIR APPLICATION IN THERAPEUTICS

[75] Inventors: Samir Jegham, Argenteuil; Jean Jacques Koenig, Maisons Laffitte; Alistair Lochead, Charenton Le Pont; Alain Nedelec, Colombes; Yves Guminski, La Garrigue, all of France

[73] Assignee: Synthelabo, Le Plessis Robinson, France

[21] Appl. No.: 662,199

[22] Filed: Jun. 12, 1996

[30] Foreign Application Priority Data

Jun. 13, 1995 [FR] France ................... 95 06951

[51] Int. Cl.$^6$ .................. C02D 487/08; A61K 31/495
[52] U.S. Cl. ........................... 514/249; 544/351
[58] Field of Search ............... 544/351; 514/249

[56] References Cited

FOREIGN PATENT DOCUMENTS

| 0 234 872 | 9/1987 | European Pat. Off. ...... C07D 307/79 |
| 93/05038 | 3/1993 | WIPO ..................... C07D 405/12 |
| 95/18104 | 7/1995 | WIPO ..................... C07D 207/09 |

*Primary Examiner*—Robert T. Bond
*Attorney, Agent, or Firm*—Foley & Lardner

[57] ABSTRACT

An optically active isomer or a racemate of a compound of general formula (I)

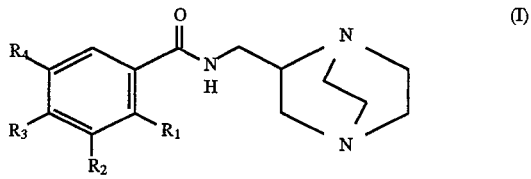

in which either $R_1$ represents a methoxy or cyclopropylmethoxy group and $R_2$ represents a hydrogen, chlorine or bromine atom, or $R_1$ and $R_2$ together form, and in this order, a group of formula —O—$CH_2$—O—, —O—$(CH_2)_2$—, —O—$(CH_2)_2$—O— or —O—$(CH_2)_3$—O—, $R_3$ represents a hydrogen atom or an amino group, and $R_4$ represents a hydrogen, chlorine or bromine atom, in the form of a free base or of a pharmaceutically acceptable acid addition salt.

12 Claims, No Drawings

N-[(1,4-DIAZABICYCLO[2.2.2] OCT-2-YL) METHYL] BENZAMIDE DERIVATIVES, THEIR PREPARATIONS AND THEIR APPLICATION IN THERAPEUTICS

The subject of the present invention is N-[(1,4-diazabicyclo[2.2.2]oct-2-yl)methyl]benzamide derivatives, their preparation and their application in therapeutics.

The compounds of the invention correspond to the general formula (I)

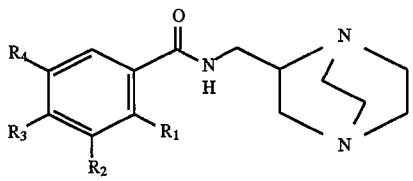

in which $R_1$ represents a methoxy or cyclopropylmethoxy group, $R_2$ represents a hydrogen, chlorine or bromine atom, or alternatively $R_1$ and $R_2$ together form, and in this order, a group of formula —O—CH$_2$—O—, —O—(CH$_2$)$_2$—, —O—(CH$_2$)$_2$—O— or —O—(CH$_2$)$_3$—O—, $R_3$ represents a hydrogen atom or an amino group, and $R_4$ represents a hydrogen, chlorine or bromine atom.

They can exist in the form of free bases or of addition salts with acids. Moreover, they contain, in the diazaoctane ring, an asymmetric carbon atom and can therefore exist in the form of optically active isomers or racemic mixtures.

As used herein, an optically active isomer is the R isomer in pure form or substantially free from the S isomer, the S isomer in pure form or substantially free from the R isomer or a mixture of the R and S isomers which contains an excess of either the R or the S isomer.

The most advantageous compounds are, in general, the compounds of general formula (I) in which $R_3$ represents an amino group and $R_4$ represents a chlorine atom.

Mention may be made, among the preferred compounds, of (+)-8-amino-7-chloro-N-[(1,4-diazabicyclo[2.2.2]oct-2-yl)methyl]-2,3-dihydro-1,4-benzodioxine-5-carboxamide, (−)-8-amino-7-chloro-N-[(1,4-diazabicyclo[2.2.2]oct-2-yl) methyl]-2,3-dihydro-1,4-benzodioxine-5-carboxamide, (+)-4-amino-5-chloro-2-(cyclopropylmethoxy)-N-[(1,4-diazabicyclo[2.2.2]oct-2-yl)methyl]benzamide, (−)-4-amino-5-chloro-2-(cyclopropylmethoxy)-N-[(1,4-diazabicyclo[2.2.2]oct-2-yl)methyl]benzamide, (−)-8-amino-7-bromo-N-[(1,4-diazabicyclo[2.2.2]oct-2-yl) methyl]-2,3-dihydro-1,4-benzodioxine-5-carboxamide, (−)-9-amino-8-chloro-N-[(1,4-diazabicyclo[2.2.2]oct-2-yl) methyl]-3,4-dihydro-2H-1,5-benzodioxepine-6-carboxamide and pharmaceutically acceptable acid addition salts thereof.

In accordance with the invention, the compounds of general formula (I) can be prepared by a process illustrated by the following scheme.

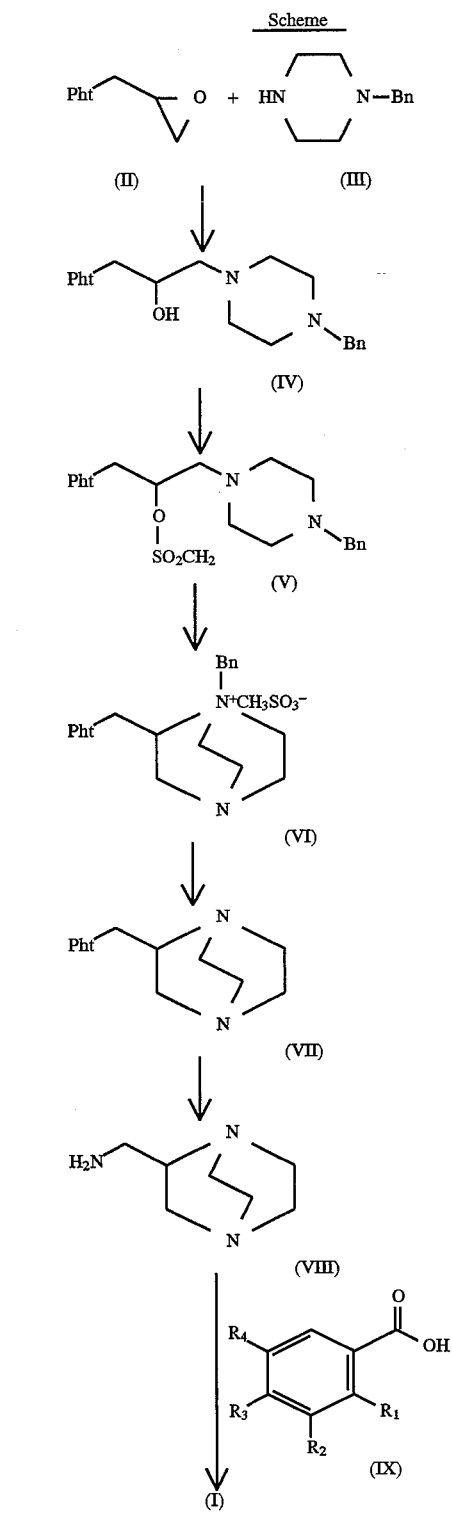

A protected aminomethyloxirane, of formula (II), in which Pht represents a phthalimido (or 1,3-dihydro-1,3-dioxo-2H-isoindol-2-yl) group, is reacted with a protected piperazine of formula (III), in which Bn represents a benzyl group, at a temperature which is typically from 80° to 120° C. The reaction typically takes place in the absence of solvent or in an aprotic solvent, for example toluene or dioxane.

An alcohol of formula (IV) is thereby obtained, which is reacted with methanesulphonyl chloride in the presence of triethylamine to give a compound of formula (V). Typically, the reaction takes place in an aprotic solvent, for example dichloromethane. Typically, the reaction takes place at a temperature of −5° to +20° C. The thus obtained compound of formula (V), is heated at a temperature which is typically about 110° C. The reaction time is typically from 2 to 8 hours. Typically, the reaction takes place in an aprotic solvent, for example toluene. A quaternary ammonium salt of formula (VI) is thereby obtained.

The ammonium salt of formula (VI) is debenzylated by catalytic hydrogenation, for example catalytic hydrogenation in the presence of palladium-on-charcoal in order to obtain a compound of formula (VII). The compound of formula (VII) is deprotected by means of hydrazine hydrate. Typically, the reaction takes place in an alcoholic solvent, for example ethanol.

Typically, the reaction takes place at a reflux temperature for 1 to 3 h.

An amine of formula (VIII) is thereby obtained. An addition salt of the amine of formula (VIII), for example the trihydrochloride, may be prepared. Finally, the compound of formula (VIII), or the addition salt thereof, is reacted with an acid of general formula (IX), in which $R_1$, $R_2$, $R_3$ and $R_4$ are as defined above. The reaction typically occurs in the presence of dicyclohexylcarbodiimide. Typically, the reaction courts in an aprotic solvent, for example pyridine. Typically, the reaction occurs at room temperature.

The thus obtained compound of formula (I) is optionally salified to give a pharmaceutically acceptable acid addition salt thereof.

The starting compound of formula (II) can be obtained from oxiranylmethyl 4-methylbenzenesulphonate and the potassium salt of 1H-isoindole-1,3(2H)-dione, which compounds are commercially available, in toluene and in the presence of a phase transfer agent such as hexadecyltributylphosphoniumbromide. The stereochemical structure of the rosylate determines that of the final compound: use of racemic tosylate results in the preparation of a racemic compound of formula (II) and use of optically active tosylate makes possible the preparation of an optically active isomer of a compound of formula (II).

Another process for the preparation of a compound of formula (II), from an optically active isomer of 2,2-dimethyl-1,3-dioxolane-4-methanol, both of which are commercially available, is illustrated in detail in the following Example 4. It consists of:

reacting an optically active isomer of 2,2-dimethyl-1,3-dioxolane-4-methanol with methanesulphonyl chloride, to obtain a corresponding (2,2-dimethyl-1,3-dioxolan-4-yl)methyl methanesulphonate;

treating the thus obtained compound with potassium phthalimide optionally in the presence of a phase transfer agent such as hexadecyltributylphosphonium bromide, to obtain a corresponding 2-[(2,2-dimethyl-1,3-dioxolan-4-yl)methyl]-1H-isoindole-1,3(2H)-dione;

treating the thus obtained compound with dilute hydrochloric acid, to obtain a corresponding 2-(2,3-dihydroxypropyl)-1H-isoindole-1,3(2H)-dione;

reacting the thus obtained compound with benzaldehyde, to obtain a corresponding 2-[(2-phenyl-1,3-dioxolan-4-yl)methyl]-1H-isoindole-1,3(2H)-dione;

reacting the thus obtained compound with N-bromosuccinimide, to obtain a corresponding 1-bromomethyl-2-(1,3-dihydro-1,3-dioxo-2H-isoindol-2-yl)ethyl benzoate; and, finally cyclizing the thus obtained compound in the presence of sodium methoxide, to give optically active 2-(oxiranylmethyl)-1H-isoindole-1,3(2H)-dione.

The benzylpiperazine of formula (III) is commercially available.

Some acids of general formula (IX) are commercially available; the others can be prepared by methods such as those described in J. Med. Chem., (1993), 36, 4121–4123 and Patent Applications EP-0234872, WO-9305038 and ES-2019042 or by saponification of corresponding esters such as those described in Patents DE-3001328 and DE-36433103.

The following examples illustrate in detail the preparation of a few compounds according to the invention. The elemental microanalyses and the IR and NMR spectra confirm the structures of the compounds obtained.

The numbers of the compounds shown between brackets in the titles correspond to those in the table given later.

EXAMPLE 1

(Compound No. 1)
(±)-4-Amino-5-chloro-N-[(1,4-diazabicyclo[2.2.2]oct-2-yl)methyl]-2-methoxybenzamide dihydrochloride.

1.1. 2-[2-Hydroxy-3-[4-(phenylmethyl)piperazin-1-yl)propyl]-1H-isoindol-1,3(2H)-dione.

34.7 g (0.197 mol) of 1-(phenylmethyl)piperazine are heated to 80° C., 40.0 g (0.197 mol) of 2-(oxiranylmethyl)-1H-isoindol-1,3 (2H)-dione are added dropwise and the mixture is heated at 100° C. for 5 min.

The mixture is allowed to cool, is taken up in 50 ml of toluene, 350 ml of heptane are added and an oil is obtained which crystallizes on cooling. After filtering and drying the crystals, 71.2 g of compound are obtained.

Melting point: 94° C.

1.2. (±)-2-(1,3-Dioxo-1,3-dihydro-2H-isoindol-2-y1)-1-[[4-(phenylmethyl)piperazin-1-yl]methyl]ethyl methanesulphonate.

A solution of 59.8 g (0.158 mol) of 2-[2-hydroxy-3-[4-(phenylmethyl)piperazin-1-yl)propyl]-1H-isoindol-1,3(2H)-dione in 350 ml of dichloromethane is cooled to 0° C. and 19.1 g (0.189 mol) of triethylamine and then, dropwise, 19.8 g (0.173 mol) of methanesulphonyl chloride are added. After 1 h, 400 ml of water are added, the organic phase is separated, the solvent is evaporated under reduced pressure and the residue is purified by chromatography on a column of silica gel, elution being carried out with a 90/10 mixture of ethyl acetate and heptane.

62.3 g of compound are obtained, which compound is used as is in the following stage.

1.3. (±)-2-(1,3-Dioxo-1,3-dihydro-2H-isoindol-2-yl)methyl-1-(phenylmethyl)-4-aza-1-azoniabicyclo[2.2.2]octane methanesulphonate.

A solution of 61 g (0.133 mol) of (±)-2-(1,3-dioxo-1,3-dihydro-2H-isoindol-2-yl)-1-[[4-(phenylmethyl)piperazin-1-yl]methyl]ethyl methanesulphonate in 500 ml of toluene is heated for 14 h at the reflux temperature, the mixture is cooled and the solid is separated by filtration, rinsed with toluene and dried.

52.9 g of compound are obtained, which compound is used as is in the following stage.

Melting point: >260° C.

1.4. (±)-2-[(1,4-Diazabicyclo[2.2.2]oct-2-yl)methyl]-2H-isoindole-1,3(2H)-dione.

A solution of 52.6 g (0.115 mol) of (±)-2-(1,3-dioxo-1,3-dihydro-2H-isoindol-2-yl)methyl-1-(phenylmethyl)-4-aza- 1-azoniabicyclo[2.2.2]octane methanesulphonate in 500 ml of methanol is placed in a hydrogenator, 15 g of 10% palladium-on-charcoal are added and catalytic hydrogenation is carried out at 50° C. under 0.1 MPa for 1 h.

The catalyst is separated by filtration, being rinsed with methanol, and the filtrate is evaporated under reduced pressure.

21.1 g of compound are obtained.

Melting point: 156° C.

1.5. (±)-1,4-Diazabicyclo[2.2.2]octane-2-methanamine trihydrochloride.

A mixture of 20.0 g (0.0737 mol) of (±)-2-[(1,4-diazabicyclo[2.2.2]oct-2-yl)methyl]-2H-isoindole-1,3(2H)-dione and 4.4 g (0.0884 mol) of hydrazine hydrate in 200 ml of ethanol is heated at reflux for 2 h 30 min.

The mixture is concentrated, the residue is taken up in 300 ml of chloroform, the insoluble material is removed by filtration, the filtrate is evaporated under reduced pressure and the residue is purified on an alumina column, solution being carried out with a 90/10/1 mixture of chloroform, methanol and aqueous ammonia. 9.3 g of yellow liquid are obtained, which liquid is distilled under reduced pressure. 8.45 g of colourless liquid are thus obtained. Boiling point: 70° C. under 100 Pa.

The trihydrochloride is prepared by dissolving 8.25 g (0.0584 mol) of this compound in 50 ml of ethanol at 10° C., 50 ml of a 4N solution of hydrochloric acid in ethanol are added, to pH=1, the solution is cooled to 0° C. and the salt which precipitates is filtered off. After drying under reduced pressure, 14.3 g of trihydrochloride are obtained.

Melting point: 280° C.

1.6. (±)-4-Amino-5-chloro-N-[(1,4-diazabicyclo[2.2.2] oct-2-yl)methyl]-2-methoxybenzamide dihydrochloride.

1.25 g (0.005 mol) of (±)-1,4-diazabicyclo[2.2.2]octane-2-methaneunine trihydrochloride are added to a solution of 0.2 g (0.005 mol) of sodium hydroxide in 1.6 ml of water, a solution of 1.11 g (0.0055 mol) of 4-amino-5-chloro-2-methoxybenzoic acid in 6.7 ml of pyridine is added dropwise, then, in two steps, and observing a time interval of 45 min, the insoluble material is removed by filtration, the filtrate is concentrated, 1.86 g (0.009 mol) of dicyclohexylcarbodiimide are added and stirring is maintained overnight at room temperature. 15 ml of water are added, stirring is carried out for 45 min, the mixture is filtered and the filtrate is evaporated under reduced pressure. The residue is taken up in water, aqueous sodium hydroxide is added to pH=10, the precipitate is collected by filtration and is purified by chromatography on a column of silica gel, elution being carried out with an 85/15/1.5 mixture of chloroform, methanol and aqueous ammonia. 1.28 g of product are obtained, which product is purified by triturating it while hot in 20 ml of ethanol. After filtration, evaporation and drying at 50° C. under reduced pressure, 1.2 g of compound are finally obtained in the base form. Melting point: 232° C.

1.0 g (0.00308 mol) of it are suspended in 10 ml of ethanol, 0.7 ml (0.008 mol) of concentrated hydrochloric acid and then 2 ml of water are added and the solution obtained is filtered and concentrated to dryness. The residue is taken up in ethanol and again concentrated to dryness. The operation is repeated and then the product is dried under reduced pressure. 0.93 g of dihydrochloride is finally obtained.

Melting point: 239° C.

EXAMPLE 2

(Compound No. 2)

(+)-4-Amino-5-chloro-N-[(1,4-diazabicyclo[2.2.2]oct-2-yl) methyl]-2-methoxybenzamide dihydrochloride.

2.1. (−)-2-(oxiranylmethyl)-1H-isoindole-1,3(2H)-dione.

A mixture of 40.75 g (0.22 mol) of potassium phthalimide, 5.07 g (0.01 mol) of hexadecyltributylphosphonium bromide and 160 ml of toluene is heated to 80° C.

45.6 g (0.2 mol) of (+)-oxiranylmethyl 4-methylbenzenesulphonate, in solution in 80 ml of toluene, are introduced over 30 min and heating is maintained between 80° and 100° C. for 2 h.

The mixture is filtered, the filtrate is washed four times with water and is dried, the solvent is evaporated under reduced pressure and the residue is crystallized from a ½ mixture of ethyl acetate and diisopropyl ether and purified by chromatography on a column of silica gel, elution being carried out with a 50/50 mixture of ethyl acetate and heptane.

28 g of product are obtained, which product is triturated in diisopropyl ether. 24.9 g of compound are obtained.

Melting point: 100° C.

$[\alpha]_D^{20} = -6°$ (c=1, CHCl$_3$).

2.2. (+)-1,4-Diazabicyclo[2.2.2]octane-2-methanamine trihydrochloride.

The procedure is as described in Examples 1.2 to 1.5, but from the optically pure (−)-2-(oxiranylmethyl)-1H-isoindole-1,3 (2H)-dione prepared in the preceding stage.

Melting point: 240 ° C. (decomposition).

$[\alpha]_D^{20} = +20.7°$ (c=1, H$_2$O).

2.3. (+)-4-Amino-5-chloro-N-[(1,4-diazabicyclo[2.2.2] oct-2-yl)methyl]-2-methoxybenzamide dihydrochloride.

The procedure is as described in Example 1.6, but from the optically pure (+)-1,4-diazabicyclo[2.2.2]octane-2-methanamine trihydrochloride prepared in the preceding stage.

Melting point: 228° C. (decomposition).

$[\alpha]_D^{20} = +14.4°$ (c=1, H$_2$O).

EXAMPLE 3

(Compound No. 3)

(−)-4-Amino-5-chloro-N-[(1,4-diazabicyclo[2.2.2]oct-2-yl) methyl]-2-methoxybenzamide dihydrochloride.

3.1. (+)-2-(Oxiranylmethyl)-1H-isoindole-1,3(2H)-dione.

The procedure is as described in Example 2.1, but from (−)-oxiranylmethyl 4-methylbenzenesulphonate.

Melting point: 97° C.

$[\alpha]_D^{20} = +8.5°$ (c=1, CH$_2$Cl$_2$).

3.2. (−)-1,4-Diazabicyclo[2.2.2]octane-2-methanamine trihydrochloride.

The procedure is as described in Examples 1.2 to 1.5, but from the optically pure (+)-2-(oxiranylmethyl)-1H-isoindole-1,3(2H)-dione prepared in the preceding stage.

Melting point: 240° C. (decomposition).

$[\alpha]_D^{20} = -22.9°$ (c=1, H$_2$O).

3.3. (−)-4-Amino-5-chloro-N-[(1,4-diazabicyclo[2.2.2] oct-2-yl)methyl]-2-methoxybenzamide dihydrochloride.

The procedure is as described in Example 1.6, but from the optically pure (−)-1,4-diazabicyclo[2.2.2]octane-2-methanamine trihydrochloride prepared in the preceding stage.

Melting point: 215° C. (decomposition).

$[\alpha]_D^{20} = -12.7°$ (c=1, H$_2$O)

EXAMPLE 4

(Compound No. 8)

(+)-8-Amino-7-chloro-N-[(1,4-diazabicyclo[2.2.2]oct-2-yl) methyl]-2,3-dihydro-1,4-benzodioxine-5-carboxamide dihydrochloride.

4.1. (−)-(2,2-Dimethyl-1,3-dioxolan-4-yl)methyl methanesulphonate.

380 ml (2.723 mol) of triethylamine are added to a solution of 300 g (2.269 mol) of (−)-2,2-dimethyl-1,3-dioxolane-4-methanol in 2.05 l of dichloromethane, the solution is cooled to −5° C. and 193 ml (2.496 mol) of methanesulphonyl chloride are added dropwise over 1 h 10. After stirring for 10 min, the solution is washed four times with water and dried and the solvent is evaporated under reduced pressure.

453 g of orange liquid product are obtained, which product is used as is in the following stage.

4.2. (+)-2-[(2,2-Dimethyl-1,3-dioxolan-4-yl)methyl]-1H-isoindole-1,3(2H)-dione.

A mixture of 398.9 g (2.154 mol) of the potassium salt of 1H-isoindole-1,3(2H)-dione and 109.3 g (0.215 mol) of hexadecyltributylphosphonium bromide in 3.25 l of toluene is heated to 60° C., 453 g (2.154 mol) of (−)-(2,2-dimethyl-1,3-dioxolan-4-yl)methyl methanesulphonate are then added dropwise over 20 min and the mixture is heated at 80° C. for 4 h. 54.7 g (0.108 mol) of hexadecyltributylphosphonium bromide are then added and heating is continued between 80° and 100° C. for 5 h.

The mixture is cooled to approximately 60° C. and washed with water and then twice with a sodium chloride solution, the organic phase is dried and the solvent is evaporated under reduced pressure.

691.6 g of orange solid product are obtained.

Melting point: 81.9°–82° C.

$[\alpha]_d^{20}$=+35.2° (c=1, $CH_2Cl_2$).

4.3. (+)-2-(2,3-Dihydroxypropyl)-1H-isoindole-1,3(2H)-dione.

A suspension of 261.3 g (2.154 mol) of (+)-2-[(2,2-dimethyl-1,3-dioxolan-4-yl)methyl]-1H-isoindole-1,3(2H)-dione, 2.8 l of water and 5.6 ml of 12M hydrochloric acid is heated at 60° C. for 2 h. The mixture is neutralized with 11 ml of 10M aqueous sodium hydroxide and 800 ml of water are evaporated off.

The residue is cooled to 12° C. and 352.9 g of white solid are obtained.

Melting point: 122.5°–122.8° C.

$[\alpha]_D^{20}$=+48.4° (c=1, $CH_3OH$).

$[\alpha]_{365}^{20}$=210.8° (c=1, $CH_3OH$).

4.4. (+)-2-[(2-Phenyl-1,3-dioxolan-4-yl)methyl]-1H-isoindole-1,3(2H)-dione

A mixture of 22.1 g (0.1 mol) of (R)-(+)-2-(2,3-dihydroxypropyl)-1H-isoindole-1,3(2H)-dione, 10.6 g (0.1 mol) of benzaldehyde, 100 ml of toluene and 0.1 g of para-toluenesulphonic acid is heated at reflux for 3 h.

The mixture is cooled and washed with water and then with an aqueous sodium hydrogencarbonate solution, the organic phase is dried, the solvent is evaporated under reduced pressure and the residue is crystallized from 100 ml of a 20/80 mixture of diethyl ether and diisopropyl ether.

25.9 g of a 50/50 mixture of diastereoisomers are obtained.

Melting point: 84° C.

$[\alpha]_D^{20}$=+62° (c=1, $CH_2Cl_2$).

4.5. (+)-1-Bromomethyl-2-(1,3-dihydro-1,3-dioxo-2H-isoindol-2-yl)ethyl benzoate.

11.2 g (0.0627 mol) of N-bromosuccinimide are added portionwise to a solution of 19.4 g (0.0627 mol) of (+)-2-[(2-phenyl-1,3-dioxolan-4-yl)methyl]-1H-isoindole-1,3(2H)-dione in 100 ml of 1,2-dichloroethane and the mixture is stirred for 2 h.

The mixture is filtered, the filtrate is washed with water containing sodium thiosulphate, the organic phase is dried, the solvent is evaporated under reduced pressure and the residue is triturated in diethyl ether.

28 g of product are obtained.

Melting point: 120° C.

$[\alpha]_D^{20}$=+57.5° (c=1, $CH_2Cl_2$).

4.6. (−)-2-(Oxiranylmethyl)-1H-isoindole-1,3(2H)-dione.

A sodium methoxide solution is prepared from 1.17 g (0.051 mol) of sodium and 15 ml of methanol and it is added, over 20 min and at 30° C., to a solution of 19.7 g (0.0507 mol) of (+)-1-bromomethyl-2-(1,3-dihydro-1,3-dioxo-2H-isoindol-2-yl)ethyl benzoate in 200 ml of toluene and the mixture is stirred at room temperature overnight.

The solution is washed with water, the solvent is evaporated under reduced pressure and the residue is triturated in a mixture of diisopropyl ether and heptane.

9.7 g of product are obtained.

Melting point: 101.4°–101.5° C.

$[\alpha]_D^{20}$=−6.6° (c=1, $CHCl_3$).

$[\alpha]_{365}^{20}$=−48.5° (c=1, $CHCl_3$).

4.7. (+)-8-Amino-7-chloro-N-[(1,4-diazabicyclo[2.2.2]oct-2-yl)methyl]-2,3-dihydro-1,4-benzodioxine-5-carboxamide dihydrochloride.

The procedure is as described in Example 1, from optically pure (−)-2-(oxiranylmethyl)-1H-isoindole-1,3(2H)-dione.

Melting point: 231° C. (decomposition).

$[\alpha]_D^{20}$=+17.8° (c=1, $H_2O$).

EXAMPLE 5

(Compound No. 9)

(−)-8-Amino-7-chloro-N-[(1,4-diazabicyclo[2.2.2]oct-2-yl) methyl ]-2,3-dihydro-1,4-benzodioxine-5-carboxamide dihydrochloride.

5.1. (+)-(2,2-Dimethyl-1,3-dioxolan-4-yl)methyl methanesulphonate.

The procedure is as described in Example 4.1, but from (+)-2,2-dimethyl-1,3-dioxolane-4-methanol.

5.2. (−)-2-[(2,2-Dimethyl-1,3-dioxolan-4-yl)methyl]-1H-isoindole-1,3(2H)-dione.

The procedure is as described in Example 4.2, from (+)-(2,2-dimethyl-1,3-dioxolan-4-yl)methyl methanesulphonate.

Melting point: 81.2°–81.3° C.

$[\alpha]_D^{20}$=−34.9° (c=1, $CH_2Cl_2$).

5.3. (−)-2-(2,3-Dihydroxypropyl)-1H-isoindole-1,3(2H)-dione.

The procedure is as described in Example 4.3, from (−)-2-[(2,2-dimethyl-1,3-dioxolan-4-yl)methyl]-1H-isoindole-1,3(2H)-dione.

Melting point: 122.8°–122.9° C.

$[\alpha]_D^{20}$=−48.8° (c=1, $CH_3OH$).

5.4. (−)-2-[(2-Phenyl-1,3-dioxolan-4-yl)methyl]-1H-isoindole-1,3(2H)-dione.

The procedure is as described in Example 4.4, from (−)-2-(2,3-dihydroxypropyl)-1H-isoindole-1,3(2H)-dione.

Melting point: 84° C.

$[\alpha]_D^{20}$=−59° (c=1, $CH_2Cl_2$).

5.5. (−)-1-Bromomethyl-2-(1,3-dihydro-1,3-dioxo-2H-isoindol-2-yl)ethyl benzoate.

The procedure is as described in Example 4.5, from (−)-2-[(2-phenyl-1,3-dioxolan-4-yl)methyl]-1H-isoindole-1,3(2H)-dione.

Melting point: 118.4°–188.6° C.

$[\alpha]_D^{20}$=−58.2° (c=1, $CH_2Cl_2$).

5.6. (+)-2-(Oxiranylmethyl)-1H-isoindole-1,3(2H)-dione.

The procedure is as described in Example 4.6, from (−)-1-bromomethyl-2-(1,3-dihydro-1,3-dioxo-2H-isoindol-2-yl)ethyl benzoate.

Melting point: 100.4°–100.5° C.

$[\alpha]_{365}^{20}=+45.5°$ (c=1, CHCl$_3$).

5.7. (−)-8-Amino-7-chloro-N-[(1,4-diazabicyclo[2.2.2]oct-2-yl)methyl]-2,3-dihydro-1,4-benzodioxine-5-carboxamide dihydrochloride.

The procedure is as described in Example 4.7, from (+)-2-(oxiranylmethyl)-1H-isoindole-1,3(2h)-dione.

Melting point: 220° C. (decomposition).

$[\alpha]_D^{20}=-16.9°$ (c=1, H$_2$O).

EXAMPLE 6

(Compound No. 20)

(−)-6-Chloro-N-[(1,4-diazabicyclo[2.2.2]oct-2-yl)methyl]-1,3-benzodioxolane-4-carboxamide dihydrochloride.

6.1. 6-Chloro-1,3-benzodioxolane-4-carboxylic acid.

A suspension of 5.0 g (30.1 mmol) of 1,3-benzodioxolane-4-carboxylic acid in 50 ml of acetic acid is prepared, it is heated to 70° C., 1.0 g of N-chlorosuccinimide is added over 15 min, heating is continued for 30 min, 1.0 g of N-chlorosuccinimide is again added and, after heating for a further 15 min, 2.0 g of N-chlorosuccinimide are added, i.e. a total of 4.0 g (30.1 mmol), and heating is maintained at 70° C. for 2 h.

The mixture is allowed to cool, is poured onto 150 ml of water and the solid is collected by filtration, washed with water and dried under vacuum.

1.72 g of solid are obtained, which solid is purified by chromatography on a column of silica gel, elution being carried out with a 95/5/0.5 mixture of dichloromethane, methanol and acetic acid. After recrystallization from a mixture of ethanol and water, 1.13 g of compound are obtained.

Melting point: 210° C.

6.2. (−)-6-Chloro-N-[(1,4-diazabicyclo[2.2.2]oct-2-yl)methyl]-1,3-benzodioxolane-4-carboxamide dihydrochloride.

The reaction is carried out with (−)-1,4-diazabicyclo[2.2.2]octane-2-methanamine as described above and the dihydrochloride of the compound obtained is prepared.

Melting point: 212° C.

$[\alpha]_D^{20}=-18°$ (c=1, H$_2$O).

The chemical structures and the physical properties of a few compounds according to the invention are illustrated in the following table. In the "R$_1$" column, C$_3$H$_5$ denotes a cyclopropyl group. In the "Salt" column, "−" denotes a compound in the form of the free base and 2HCl denotes a dihydrochloride.

In the "M.p. (°C.)" column, (d) denotes a melting point with decomposition.

In the "$[\alpha]_D^{20}$" column, the optical rotation is determined at c=1, H$_2$O for the dihydrochlorides and at c=1, CH$_3$OH for the bases (Compounds No. 12, 13 and 19). The value 0 denotes a racemate.

TABLE

| No. | R$_1$ | R$_2$ | R$_3$ | R$_4$ | Salt | M.p. (°C.) | | $[\alpha]_D^{20}$ |
|---|---|---|---|---|---|---|---|---|
| 1 | −OCH$_3$ | H | NH$_2$ | Cl | 2HCl | 239 | | 0 |
| 2 | −OCH$_3$ | H | NH$_2$ | Cl | 2HCl | 228 | (d) | +14.4 |
| 3 | −OCH$_3$ | H | NH$_2$ | Cl | 2HCl | 215 | | −12.7 |
| 4 | −OCH$_3$ | H | H | Cl | 2HCl | 223 | | +12.7 |
| 5 | −OCH$_3$ | H | NH$_2$ | H | 2HCl | 210−235 | (d) | +8.7 |
| 6 | −O−(CH$_2$)$_2$− | | H | Cl | 2HCl | 197−250 | (d) | +8.1 |
| 7 | −O−(CH$_2$)$_2$− | | H | Cl | 2HCl | 229−265 | | −13.8 |
| 8 | −O−(CH$_2$)$_2$−O− | | NH$_2$ | Cl | 2HCl | 231 | (d) | +17.8 |
| 9 | −O−(CH$_2$)$_2$−O− | | NH$_2$ | Cl | 2HCl | 220 | (d) | −16.9 |
| 10 | −OCH$_2$cC$_3$H$_5$ | H | NH$_2$ | Cl | 2HCl | 210−215 | (d) | +7.9 |
| 11 | −OCH$_2$cC$_3$H$_5$ | H | NH$_2$ | Cl | 2HCl | 220−230 | | −12.0 |
| 12 | −OCH$_3$ | Cl | NH$_2$ | Cl | — | 212−255 | | +23.5 |
| 13 | −OCH$_3$ | Cl | NH$_2$ | Cl | — | 212−255 | | −22.8 |
| 14 | −OCH$_3$ | Br | NH$_2$ | Br | 2HCl | 230 | | +12.5 |
| 15 | −OCH$_3$ | Br | NH$_2$ | Br | 2HCl | 195 | | −10.8 |
| 16 | −O−(CH$_2$)$_2$−O− | | H | Cl | 2HCl | 253−254 | | +20.0 |
| 17 | −O−(CH$_2$)$_2$−O− | | H | Cl | 2HCl | 220 | | −18.5 |
| 18 | −O−(CH$_2$)$_2$−O− | | NH$_2$ | Br | 2HCl | 226−228 | | −16.5 |
| 19 | −O−(CH$_2$)$_3$−O− | | NH$_2$ | Cl | — | 214 | | −24.6 |
| 20 | −O−CH$_2$−O− | | H | Cl | 2HCl | 212 | | −18.0 |

The compounds of the invention have formed the subject of tests which demonstrated their advantage as substances possessing therapeutic activities.

Their affinity for 5-H$_3$ serotoninergic receptors has thus been demonstrated by the displacement of the binding of a labelled specific ligand, [$^3$H]-(S)-zacopride. The study is carried out in vitro on the 5-HT$_3$ receptors of the rat cortex, essentially as described by Barnes N. M. et al., *J. Pharm. Pharmacol.*, (1988) 40, 548–551. Male Sprague-Dawley rats (OFA, Iffa Credo, Lyons, France), weighting from 200 to 250 g, are humanely killed and the brain is removed. The cortex is then dissected and homogenized using a Polytron® mill (7.20 s position) in 20 volumes of Tris buffer (25 mM, pH =7.4 at 22° C.), the homogenate is centrifuged at 45,000 g for 10 min using a Sorvall® centrifuge equipped with an SS34 rotor and the pellet is resuspended in 10 volumes of Tris buffer and incubated at 37° C. for 10 min with agitation.

The suspension is diluted to 20 volumes using Tris buffer and recentrifuged under the same conditions and the pellet is then resuspended in 5 volumes of Tris buffer and divided into 5 ml aliquot fractions which are frozen at −80° C.

On the day of the experiment, the preparation is defrosted at +4° C. and then diluted 1.2 times using Tris-NaCl incubation buffer (25 mM Tris, 150 mM NaCl, pH=7.4 at 22° C.).

The membrane suspension (100 μl, 1 mg of proteins) is then incubated at 25° C. for 25 min in the presence of 0.5 nM of [$^3$H]-(S)-zacopride (specific activity 75–85 Ci/mmol, Amersham, Little Chalfont, Great Britain) in a final volume of 500 μl of Tris-NaCl buffer in the presence or in the absence of test compound.

Incubation is halted by filtration through Whatman GF/B filters pretreated with 0.1% polyethyleneimine. Each reaction tube is prediluted with 4 ml of Tris-NaCl buffer and then rinsed three times with 4.5 ml Tris-NaCl buffer.

The filters are cut up beforehand before drying in an oven (120° C., 5 min). The radioactivity retained on the filters is determined by liquid scintigraphy. The non-specific binding is determined in the presence of 10 μM of MDL 72222 (ligand described in the cited article). For each concentration of studied compound, the percentage of inhibition of the specific binding of [$^3$H]-(S)-zacopride and then the IC$_{50}$ concentration, the concentration of this compound which inhibits 50 % of this specific binding, are determined.

The IC$_{50}$ values of the compounds of the invention lie between 0.009 and 1 μM.

The compounds of the invention were also studied for their affinity with respect to 5-HT$_4$ receptors in the striatum of guinea pigs according to the method described by Grossman et al. in Br. J. Pharmacol., (1993) 109, 618–624.

Guinea pigs (Hartley, Charles River, France) weighing 300 to 400 g are humanely killed, the brains are removed and the striata are excised and frozen at −80° C.

On the day of the experiment, the tissue is defrosted at +4° C. in 33 volumes of HEPES-NaOH buffer (50 mM, pH=7.4 at 20° C.) and is homogenized using a Polytron® mill, the homogenate is centrifuged at 48,000 g for 10 min, the pellet is recovered, resuspended and recentrifigued under the same conditions and the final pellet is resuspended in HEPES-NaOH, in the proportion of 30 mg of tissue per ml.

100 μl of this membrane suspension are incubated at 0° C. for 120 min in the presence of [$^3$H]GR113808 (ligand described in the cited article, specific activity 80–85 Ci/mmol) in a final volume of 1 ml of HEPES-NaOH buffer (50 mM, pH=7.4), in the presence or in the absence of test compound. Incubation is halted by filtration through a Whatman GF/B filter pretreated with 0.1% polyethyleneimine, each tube is rinsed with 4 ml of buffer at 0° C., filtration is again carried out and the radioactivity retained on the filter is measured by liquid scintigraphy.

The non-specific binding is determined in the presence of 30 μM serotonin. The specific binding represents 90% of the total radioactivity recovered on the filter.

For each concentration of studied compound, the percentage of inhibition of the specific binding of [$^3$H]GR113808 and then the IC$_{50}$, the concentration of the tested compound which inhibits 50% of the specific binding, are determined.

The IC$_{50}$ values of the compounds of the invention lie between 0.008 and 1 μM.

The compounds of the invention were also studied as regards their agonist or antagonist effects with respect to 5-HT$_4$ receptors in the rat oesophagus, according to the method described by Baxter et al. in Naunyn Scbauied. Arch. Pharmacol., (1991) 343, 439. Male Sprague-Dawley rats weighing from 300 to 450 g are used. An approximately 1.5 cm fragment is quickly removed from the end part of the oesophagus, the muscular layer is removed and the internal muscular mucosal tunic is opened longitudinally, mounted in an isolated organ vessel containing a Krebs-Henseleit solution at 32° C. oxygenated by a carbogen stream (95% O$_2$ and 5% CO$_2$) and connected to an isometric transducer under a basal tension of 0.5 g. A contraction of the tissue is induced by the addition of 0.5 μM of carbachol, there is a wait while the contraction becomes stabilized (15 min), and then the preparation is exposed to serotonin (1 μM) in order to quantify the maximum relaxation. The tissue is washed and, after a period of 20 min, 0.5 μM of carbachol is again added and the preparation is exposed to the study compound, in increasing additive doses from 0.1 to 1 μM. The compounds which induce a relaxation are characterized as 5-HT$_4$ agonists.

For the compounds which do not induce relaxation, the preparation is exposed to serotonin in increasing additive concentrations, from 0.1 nM to a concentration inducing a maximum relaxation, and the relaxation curve due to serotonin, in the presence of the study compound, is then compared with a control curve prepared in the absence of the said compound. If its presence induces a shift of the curve towards the right, the study compound is characterized as a 5-HT$_4$ antagonist.

Finally, the compounds of the invention were studied as regards their antagonist effects with respect to 5-HT$_3$ receptors of the descending colon smooth muscle isolated from the guinea pig, according to the method described by Grossman et al. in Br. J. Pharmacol., (1989) 97, 451.

Serotonin (0.1–100 μM), after blockage of the receptors of 5-HT$_1$ and 5-HT$_2$ types (0.1 μM methysergide) and desensitization of 5-HT$_4$ receptors (10 μM 5-methoxy-tryptamine), causes a contraction, dependent on the concentration, of the smooth muscular part of the guinea pig descending colon, by stimulation of 5-HT$_3$ receptors. The contractions are recorded by isometry. The antagonist effect of a compound on 5-HT$_3$ serotoninergic receptors is quantified by the measurement of the shift of an effect-control concentration of serotonin curve (successive increasing non-additive concentrations), at concentrations of the compound of between 1 nM and 0.1 μM, with an incubation of 30 min.

The results of the biological tests carried out on the compounds of the invention show that they are ligands for serotoninergic receptors of 5-HT$_3$ and/or 5-HT$_3$ types and that they act as 5-HT$_3$ agonists or antagonists and/or as 5-HT$_3$ antagonists.

The compounds can therefore be used for the treatment and prevention of disorders in which 5-HT$_3$ and/or 5-HT$_4$ receptors are involved, whether at the level of the central nervous system, of the gastrointestinal system, of the cardiovascular system or of the urinary system.

At the level of the central nervous system, these disorders and problems comprise in particular neurological and psychiatric disorders such as cognitive disorders, psychoses, compulsive and obsessional beharlouts and states of depression and of anxiety. The cognitive disorders comprise, for example, memory and attention deficits, states of dementia (senile dementias of the Alzheimer's disease type or dementias related to age), cerebrovascular deficiencies or Parkinson's disease. The psychoses comprise, for example, paranoia, schizophrenia, mania and autism. The compulsive and obsessional behaviours comprise, for example, eating disorders of the loss of appetite or bulimia type. The states of depression and of anxiety comprise, for example, anxieties of anticipatory type (before a surgical operation, before dental treatment, and the like), the anxiety caused by dependence on or withdrawal from alcohol or drugs, mania, seasonal affective disorders, migraines or nauseas.

At the level of the gastrointestinal system, these disorders and problems comprise in particular vomiting induced by an anti-tumour treatment, direct or indirect disorders of gastro-motility of the oesophagus, of the stomach or of the intestines, or specific complaints, such as dyspepsia, ulcer, gastro-oesophagal reflux, flatulence, irritable bowel syndrome, disorders of intestinal secretion or diarrhoeas, for example those induced by cholera or by carcinoid syndrome.

At the level of the cardiovascular system, these disorders and problems comprise in particular pathologies related, directly or indirectly, to cardiac arrhythmias.

At the level of the urinary system, these disorders and problems comprise in particular incontinences of all sorts, as well as their causes or consequences, for example infections, stones or renal damage.

The compounds of the invention can be presented in all forms of compositions appropriate for enteral or parenteral administration, such as tablets, dragées, capsules, including hard gelatin capsules, suspensions or solutions to be swallowed or injected, such as syrups or phials, and the like, in combination with suitable excepients, and in doses which make possible a daily administration of 0.005 to 20 mg/kg.

We claim:

1. An optically active isomer or a racemate of a compound of formula (I)

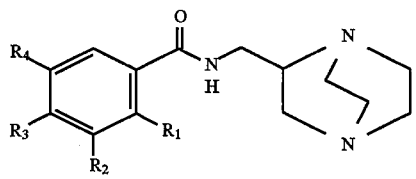

in which either $R_1$ represents a methoxy or cyclopropylmethoxy group and $R_2$ represents a hydrogen, chlorine or bromine atom, or $R_1$ and $R_2$ together form, and in this order, a group of formula —O—$CH_2$—O—, —O—$(CH_2)_2$—, —O—$(CH_2)_2$—O— or —O—$(CH_2)_3$—O—, $R_3$ represents a hydrogen atom or an amino group, and $R_4$ represents a hydrogen, chlorine or bromine atom, in the form of a free base or of a pharmaceutically acceptable acid addition salt.

2. The compound of claim 1 in which $R_3$ represents an amino group and $R_4$ represents a chlorine atom, or a pharmaceutically acceptable acid addition salt thereof.

3. A compound of claim 1, which is (+)-8-amino-7-chloro-N-[(1,4-diazabicyclo[2.2.2]oct-2-yl)methyl]-2,3-dihydro-1,4-benzodioxine-5-carboxamide, in the form of a free base or of a pharmaceutically acceptable addition salt with an acid.

4. A compound of claim 1, which is (−)-8-amino-7-chloro-N-[(1,4-diazabicyclo[2.2.2]oct-2-yl)methyl]-2,3-dihydro-1,4-benzodioxine-5-carboxamide, in the form of a free base or of a pharmaceutically acceptable addition salt with an acid.

5. A compound of claim 1, which is (+)-4-amino-5-chloro-2-(cyclopropylmethoxy)-N-[(1,4-diazabicyclo[2.2.2]oct-2-yl)methyl]benzamide, in the form of free base or of a pharmaceutically acceptable addition salt with an acid.

6. A compound of claim 1, which is (−)-4-amino-5-chloro-2-(cyclopropylmethoxy)-N-[(1,4-diazabicyclo[2.2.2]oct-2-yl)methyl]benzamide, in the form of a free base or of a pharmaceutically acceptable addition salt with an acid.

7. A compound of claim 1, which is (−)-8-amino-7-bromo-N-[(1,4-diazabicyclo[2.2.2]oct-2-yl)methyl]-2,3-dihydro-1,4-benzodioxine-5-carboxamide, in the form of a free base or of a pharmaceutically acceptable addition salt with an acid.

8. A compound of claim 1, which is (−)-9-amino-8-chloro-N-[(1,4-diazabicyclo[2.2.2]oct-2-yl)methyl]-3,4-dihydro-2H-1,5-benzodioxepine-6-carboxamide, in the form of a free base or of a pharmaceutically acceptable addition salt with an acid.

9. A process for the preparation of a compound according to claim 1, which process comprises:

reacting a protected aminomethyloxirane of formula (II)

in which Pht represents a phthalimido group, with a protected piperazine of formula (III)

in which Bn represents a benzyl group, in order to obtain an alcohol of formula (IV);

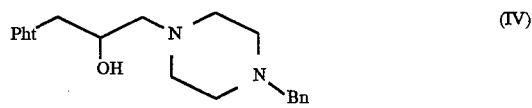

reacting the alcohol of formula (IV) with methanesulphonyl chloride in the presence of triethylamine to obtain a compound of formula (V);

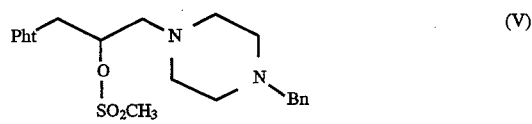

heating the compound of formula (V) to obtain a quaternary ammonium salt of formula (VI);

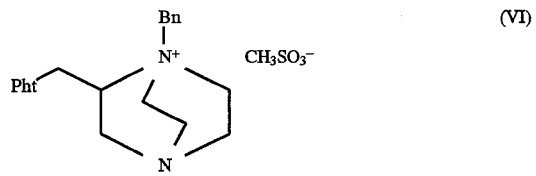

debenzylating the compound of formula (VI) by catalytic hydrogenation, to obtain a compound of formula (VII);

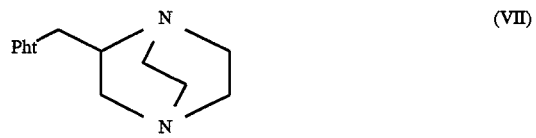

deprotecting the compound of formula (VII) using hydrazine hydrate, to obtain an amine of formula (VIII);

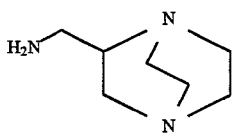

reacting the amine of formula (VIII) with an acid of formula (IX)

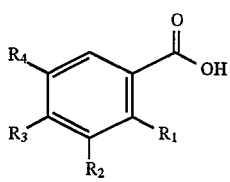

in which $R_1$, $R_2$, $R_3$ and $R_4$ are as defined in claim 1, to obtain a compound of formula (I) as defined in claim 1; and optionally salifying the thus obtained compound of formula (I) to give a pharmaceutically acceptable acid addition salt thereof.

10. The process of claim 9, in which the compound of formula (II) is an optically active isomer of 2-(oxiranylmethyl)-1H-isoindole-1,3(2H)-dione and is prepared by:

reacting an optically active isomer of 2,2-dimethyl-1,3-dioxolane-4-methanol with methanesulphonyl chloride to obtain the corresponding (2,2-dimethyl-1,3-dioxolan-4-yl)methyl methanesulphonate;

treating the thus obtained compound with potassium phthalimide, to obtain a corresponding 2-[(2,2-dimethyl-1,3-dioxolan-4-yl)methyl]-1H-isoindole-1,3(2H)-dione;

treating the thus obtained compound with dilute hydrochloric acid, to obtain a corresponding 2-(2,3-dihydroxypropyl)-1H-isoindole-1,3(2H)-dione;

reacting the thus obtained compound with benzaldehyde, to obtain a corresponding 2-[(2-phenyl-1,3-dioxolan-4-yl)methyl]-1H-isoindole-1,3(2H)-dione;

reacting the thus obtained compound with N-bromosuccinimide, to obtain a corresponding 1-bromomethyl-2-(1,3-dihydro-1,3-dioxo-2H-isoindol-2-yl)ethyl benzoate; and, finally, cyclizing the thus obtained compound in the presence of sodium methoxide, to give optically active 2-(oxiranylmethyl)-1H-isoindole-1,3(2H)-dione.

11. A pharmaceutical composition, comprising a compound according to claim 1, or a pharmaceutically acceptable acid addition salt thereof in combination with an excipient.

12. A method of treating a subject, wherein the subject is suffering from, or is susceptible to, a disorder in which $5\text{-}H_3$, and/or $5\text{-}H_4$ receptors are involved, comprising administering to said subject an effective amount of a compound of formula (I), as defined in claim 1, or a pharmaceutically acceptable acid addition salt thereof.

* * * * *